(12) United States Patent
Wang et al.

(10) Patent No.: US 9,931,367 B2
(45) Date of Patent: Apr. 3, 2018

(54) USES OF CISTANCHE TUBULOSA EXTRACT AND ISOACTEOSIDE IN PROTECTING MUSCLE

(71) Applicant: SINPHAR TIAN-LI PHARMACEUTICAL CO., LTD. (HANGZHOU), Hangzhou, Zhejiang (CN)

(72) Inventors: Chao-Jih Wang, Zhejiang (CN); Ai-Ling Yeh, Yilan County (TW)

(73) Assignee: SINPHAR TIAN-LI PHARMACEUTICAL CO., LTD. (HANGZHOU), Hangzhou, Zhejiang (CN)

( * ) Notice: Subject to any disclaimer, the term of this patent is extended or adjusted under 35 U.S.C. 154(b) by 0 days.

(21) Appl. No.: 15/403,977

(22) Filed: Jan. 11, 2017

(65) Prior Publication Data

US 2017/0196926 A1  Jul. 13, 2017

Related U.S. Application Data

(60) Provisional application No. 62/277,795, filed on Jan. 12, 2016.

(51) Int. Cl.
*A61K 36/64* (2006.01)

(52) U.S. Cl.
CPC ................................ *A61K 36/64* (2013.01)

(58) Field of Classification Search
None
See application file for complete search history.

(56) References Cited

U.S. PATENT DOCUMENTS 7,087,252 B2 * 8/2006 Tu ........................ A61K 31/70
424/725
2011/0144040 A1 6/2011 Wells et al.

FOREIGN PATENT DOCUMENTS

CN  101554451  10/2009

OTHER PUBLICATIONS

Run-Lan Cai et al., "Antifatigue activity of phenylethanoid-rich extract from Cistanche deserticola", Phytotherapy Research, 2010, vol. 24, Issue 2, pp. 313-315.
Han Lichun et al., "Effects of Cistanche deserticola Y.C. Ma on Serum Creatine Kinase and Ultrastructures of Skeletal Muscles in Mice", China Journal of Chinese Materia Medica, 1993, vol. 18(12), pp. 743-745.
Hai-Tao Zhou et al., "Effect of Cistanches Herba on the Swimming Ability and Oxidation Resistance of Mitochondrial in Rats", Chinese Journal of Experimental Traditional Medical Formulae, 2012, vol. 18(6), pp. 229-235 (English Abstract).
Qijun Luo et al., "Protective Effect of Cistanche Deserticola on Skeletal Muscle Oxidative Injury in High Intensity Training Rats", Journal of Zhanjiang Normal College, 2012, vol. 33(3), pp. 1-4 (English Abstract).
International Search Report and Written Opinion of International Application No. PCT/CN2017/070862 dated Mar. 31, 2017.

* cited by examiner

*Primary Examiner* — Susan Hoffman
(74) *Attorney, Agent, or Firm* — Ping Wang; Andrews Kurth Kenyon LLP (57) ABSTRACT

Use of *Cistanche tubulosa* extract, isoacteoside and/or a pharmaceutical acceptable salt of isoacteoside in the manufacture of a medicament or a food product for protecting muscles, wherein the medicament is particularly used for protecting muscle cells against injury to regulate, treat and/or delay muscle loss, and especially for the muscle loss caused by aging, diseases, and/or cochexia. The food product is a health food, a nutritional supplement food, or a special nutrition food.

6 Claims, 10 Drawing Sheets

USES OF CISTANCHE TUBULOSA EXTRACT AND ISOACTEOSIDE IN PROTECTING MUSCLE

CROSS REFERENCE TO RELATED APPLICATIONS

This application claims priority from U.S. Provisional Application Ser. No. 62/277,795 filed on Jan. 12, 2016 with the United States Patent and Trademark Office, the disclosures of which are incorporated herein in their entirety by reference.

FIELD OF THE INVENTION

The present invention relates to the uses of a *Cistanche tubulosa* extract and isoacteoside (i.e., an ingredient of the *Cistanche tubulosa* extract) or a pharmaceutically acceptable salt of isoacteoside. The invention especially relates to the use of the *Cistanche tubulosa* extract, isoacteoside or a pharmaceutically acceptable salt of isoacteoside in protecting muscles, including protecting muscle cells against injury and thereby regulating, treating, and/or delaying muscle loss, especially muscle loss caused by aging, diseases, and/or cachexia.

BACKGROUND OF THE INVENTION

Muscle tissue is the most abundant tissue in mammals, and is mainly responsible for generating force to cause movement of various parts of the body. Muscle can be divided into three groups: skeletal muscle, cardiac muscle and smooth muscle. Based on the metabolic types and characteristics, skeletal muscle can be divided into slow twitch muscle and fast twitch muscle, wherein the former consists of slow-twitch fiber proteins that can twitch for a longer period, but the generated force is weaker; the latter consists of fast-twitch fiber proteins that can twitch faster and stronger than the former, but fatigues more easily.

Under normal physiological conditions, there is a dynamic balance between the synthesis and degradation of muscle proteins. However, when an imbalance of muscle protein metabolism occurs (namely, the degradation rate of muscle proteins become greater than the synthesis rate), it causes loss of muscle. Severe muscle loss leads to muscle atrophy and characteristic changes, such as a decrease in muscle mass, a reduction of muscle fiber cross-sectional area, and a selective reduction of muscle fiber type-related proteins (i.e., slow-twitch fiber proteins and fast-twitch fiber proteins), which can result in symptoms that seriously affect daily work and vital function, including a reduction in muscle strength, movement disorders, fatigue, metabolic disturbances, etc.

It is known that muscle cell injury can be caused by various physiology conditions or specific diseases that lead to muscle cell metabolic disturbance or apoptosis of muscle cells, causing muscle loss. Factors leading to muscle loss include, for example, neurodegeneration, long-term bed rest, aging, diseases, cachexia (e.g., cancer cachexia), etc., wherein the diseases include sepsis, acquired immune deficiency syndrome (AIDS), renal failure, Cushing syndrome (CS), sarcopenia, cancer, chronic obstructive pulmonary disease (COPD), congestive heart failure (CHF), trauma, etc.

Aging is the major factor causing sarcopenia. Statistical data indicate that the incidence rate of sarcopenia among those aged 60~70 is 13 to 24%, while the incidence rate of sarcopenia among people older than 80 years of age is about 50%. Besides, in America, the medical costs caused by sarcopenia per year is about 11.8 to 26.2 billion USD. While cachexia relates to other diseases having high incidence rates, for example, about 50% of patients with cancer, 20 to 40% of patients with COPD, and 50 to 70% of patients with CHF will exhibit the symptoms of cachexia (e.g., dystrophy).

Herba *Cistanches* was firstly recorded and rated as a top-grade herbal remedy in "Shennong Bencaojing" (The Classic of Herbal Medicine). Herba *Cistanches* is effective in nourishing the kidneys and invigorating yang, boosting essence and blood, lubricating the bowels to relieve constipation, making it the Chinese medicine prescribed most frequently by physicians for kidney nourishment and yang invigoration. *Cistanche tubulosa* is a kind of perennial parasitic herb belonging to the family of Orobanchaceae and the genus of *Cistanche*, which is found in the desert and other dry areas and subsists on absorbing nutrients from its host plant, Red willow. That is, *Cistanche tubulosa* is a precious and rare medicinal material. *Cistanche tubulosa* association with, for example, renal function improvement, memory enhancement, immune function regulation, anti-dementia disease, anti-aging, and anti-fatigue were published in "Pharmacopoeia of the People's Republic of China" in 2005.

In the clinical practice, there is still a lack of an effective method for treating or delaying muscle loss, and the effects of *Cistanche tubulosa* on protecting muscle against atrophy have not been presented on any documents so far. Therefore, to develop a more effective method for treating or delaying muscle loss, the inventors of the present invention selected *Cistanche tubulosa* from the traditional herba, and then investigated the feasibility of using *Cistanche tubulosa* in protecting muscle (namely, protecting muscle cells against injury and preventing muscle loss). The inventors of the present invention found that the *Cistanche tubulosa* extract and isoaceteoside contained therein are effective in protecting muscle cells against injury. Therefore, the *Cistanche tubulosa* extract and isoaceteoside can be used for regulating, treating and/or delaying muscle loss, especially for regulating, treating and/or delaying muscle loss caused by aging, disease and/or cachexia, and thus can be used for providing a pharmaceutical composition, a medicament or a food product that can protect muscles.

SUMMARY OF THE INVENTION

An objective of the present invention is to provide a use of *Cistanche tubulosa* extract in the manufacture of a medicament or a food product for protecting muscles. Preferably, the *Cistanche tubulosa* extract is a polar solvent extract of *Cistanche tubulosa*, wherein the polar solvent is selected from the group consisting of water, C1-C4 alcohols, and combinations thereof. More preferably, the *Cistanche tubulosa* extract comprises isoacteoside. The medicament is used for protecting muscle cells against injury, or for treating and/or delaying muscle loss caused by at least one of the following: aging, disease, and cachexia. The food product is used for regulating muscle loss caused by at least one of the following: aging, disease, and cachexia, and is useful for helping normal muscle contraction, maintaining normal muscle physiology, maintaining normal neuromuscular function, maintaining normal energy metabolism, or enhancing energy. And the food product is a health food, a nutritional supplement food or a special nutrition food.

Another objective of the present invention is to provide a use of an active ingredient in the manufacture of a medicament or a food product for protecting muscles, wherein the active ingredient is isoacteoside and/or a pharmaceutically acceptable salt of isoacteoside. Preferably, the active ingredient is used in the form of a plant extract; more preferably, the active ingredient is used in the form of a *Cistanche tubulosa* extract, especially a polar solvent extract of *Cistanche tubulosa*, wherein the polar solvent is selected from the group consisting of water, C1-C4 alcohols, and combinations thereof. The medicament is used for protecting muscle cells against injury, or for treating and/or delaying muscle loss caused by at least one of the following: aging, disease, and cachexia. The food product is used for regulating muscle loss caused by at least one of the following: aging, disease, and cachexia, and is useful for helping normal muscle contraction, maintaining normal muscle physiology, maintaining normal neuromuscular function, maintaining normal energy metabolism, or enhancing energy. And the food product is a health food, a nutritional supplement food or a special nutrition food.

Still another objective of the present invention is to provide a method for protecting muscles, comprising administering to a subject in need an effective amount of a *Cistanche tubulosa* extract. Preferably, the *Cistanche tubulosa* extract is a polar solvent extract of *Cistanche tubulosa*, wherein the polar solvent is selected from the group consisting of water, C1-C4 alcohols, and combinations thereof. More preferably, the *Cistanche tubulosa* extract comprises isoacteoside. The method is for protecting muscle cells against injury, and for regulating, treating, and/or delaying muscle loss caused by at least one of the following: aging, disease, and cachexia, or it is for helping normal muscle contraction, maintaining normal muscle physiology, maintaining normal neuromuscular function, maintaining normal energy metabolism, or enhancing energy.

Yet another objective of the present invention is to provide a method for protecting muscles, comprising administering to a subject in need an effective amount of an active ingredient, wherein the active ingredient is isoacteoside and/or a pharmaceutically acceptable salt of isoacteoside. Preferably, the active ingredient is used in the form of a plant extract; more preferably, the active ingredient is used in the form of a *Cistanche tubulosa* extract, especially a polar solvent extract of *Cistanche tubulosa*, wherein the polar solvent is selected from the group consisting of water, C1-C4 alcohols, and combinations thereof. The method is for protecting muscle cells against injury, and for regulating, treating, and/or delaying muscle loss caused by at least one of the following: aging, disease, and cachexia, or it is for helping normal muscle contraction, maintaining normal muscle physiology, maintaining normal neuromuscular function, maintaining normal energy metabolism, or enhancing energy.

Still yet another objective of the present invention is to provide a composition for protecting muscles, wherein the composition is a medicament or a food product comprising an effective amount of the *Cistanche tubulosa* extract. Preferably, the *Cistanche tubulosa* extract is a polar solvent extract of *Cistanche tubulosa*, wherein the polar solvent is selected from the group consisting of water, C1-C4 alcohols, and combinations thereof. More preferably, the *Cistanche tubulosa* extract comprises isoacteoside. The composition is for protecting muscle cells against injury, and for regulating, treating, and/or delaying muscle loss caused by at least one of the following: aging, disease, and cachexia, or it is for helping normal muscle contraction, maintaining normal muscle physiology, maintaining normal neuromuscular function, maintaining normal energy metabolism, or enhancing energy.

Still yet another objective of the present invention is to provide a composition for protecting muscles, wherein the composition is a medicament or a food product comprising an effective amount of an active ingredient, and the active ingredient therein is isoacteoside and/or a pharmaceutically acceptable salt of isoacteoside. Preferably, the active ingredient is used in the form of a plant extract; more preferably, the active ingredient is used in the form of a *Cistanche tubulosa* extract, especially a polar solvent extract of *Cistanche tubulosa*, wherein the polar solvent is selected from the group consisting of water, C1-C4 alcohols, and combinations thereof. The composition is for protecting muscle cells against injury, and for regulating, treating, and/or delaying muscle loss caused by at least one of the following: aging, disease, and cachexia, or it is for helping normal muscle contraction, maintaining normal muscle physiology, maintaining normal neuromuscular function, maintaining normal energy metabolism, or enhancing energy.

The detailed technology and some particular embodiments implemented for the present invention are described in the following paragraphs for people skilled in this field to well appreciate the features of the claimed invention.

DESCRIPTION OF THE PREFERRED EMBODIMENTS

The detailed technology and preferred embodiments implemented for the present invention are described in the following paragraphs for people skilled in this field to well appreciate the features of the claimed invention. However, the present invention may be realized in various embodiments without departing from the spirit of the present invention, and the present invention should not be considered to be limited to the embodiments described in the specification. In addition, unless otherwise state herein, the expressions "a," "the" or the like recited in the specification of the present invention (especially in the claims) should include both the singular and plural forms. Furthermore, the term "an effective amount" used in this specification refers to the amount of the compound that can at least partially alleviate the condition that is being treated in a suspected subject when administered to the subject. The term "subject" refers to a mammalian, including human and non-human animals. The term "treat" or "treating" includes the prevention of particular diseases and/or disorders, the amelioration of particular diseases and/or disorders, and/or the prevention or elimination of the diseases and/or disorder. The unit "mg/kg-body weight" refers the dosage in mg required per kg of body weight.

The numerical ranges (e.g., 5 to 100) used in this specification should be construed as including all of the rational numbers in the ranges and ranges consisting of any rational numbers in the ranges. Therefore, the numerical ranges used in this specification should include all the possible combinations of numerical values between the lowest value and the highest value listed therein. In addition, the word "about", "approximately" or "almost" as used herein substantially represents values within ±20% of the stated value, preferably within ±10% and more preferably within ±5%.

In this specification, the term "pharmaceutically acceptable salt" refers to salts that can produce pharmacological activities that are the same as or similar to those produced by their parent compound after being administrated to an organism and that are physiologically tolerable (i.e., with a toxicity as low as possible).

The inventors of the present invention found that the *Cistanche tubulosa* extract can effectively protect muscle cells against injury, and thus can be used for protecting muscles. The *Cistanche tubulosa* extract has the effect of treating and/or delaying muscle loss. Without being limited by the theory, it is believed that the *Cistanche tubulosa* extract used in the present invention can effectively regulate, treat, and/or delay muscle loss caused by at least one of the following: aging, disease, and cachexia. Therefore, the present invention provides uses of the *Cistanche tubulosa* extract in protecting muscles, comprising a use of the *Cistanche tubulosa* extract in the manufacture of a medicament or a food product for protecting muscles, a method for protecting muscles comprising administrating the *Cistanche tubulosa* extract to a subject in need, and a food product or a pharmaceutical composition comprising the *Cistanche tubulosa* extract.

According to the present invention, the *Cistanche tubulosa* extract provided by the method comprising the following steps can be employed: (a) extracting *Cistanche tubulosa* with a polar solvent to provide an extract solution; and (b) optionally drying the extract solution. The polar solvent is water and/or a C1-C4 alcohol. The polar solvent is preferably water, ethanol, or a combination thereof. The amount of the polar solvent and *Cistanche tubulosa* may be optionally adjusted. In general, the volume ratio between the polar solvent and *Cistanche tubulosa* may range from about 1:1 to about 50:1, and preferably about 5:1 to about 20:1.

According to the present invention, there is no limitation on the parts of *Cistanche tubulosa* for use in providing the *Cistanche tubulosa* extract. For example, the *Cistanche tubulosa* extract can be provided by extracting the stem, flower, or the whole plant of *Cistanche tubulosa*. According to one embodiment of the present invention, the succulent stems of *Cistanche tubulosa* were used to provide the extract.

In step (a), the extraction is carried out for a period of time to achieve the desired extraction efficiency. For example, when water is used as the polar solvent, the extraction time is usually at least 15 minutes, preferably at least 30 minutes, and more preferably at least 60 minutes. Optionally, the extraction may be accompanied with other operations (e.g., stewing, cooling, filtration, concentration under reduced pressure, and resin column chromatography, etc.). Optionally, one may repeat the extraction step (a) one or more times with the same or different solvent(s) before performing step (b), and combine all the liquid phase thus obtained to provide the extract solution for step (b); alternatively, one may repeat the cycle of extraction step (a), extraction step (b) and the other optional operations as mentioned above to achieve as much extraction efficiency as possible, such as the preparation method of the *Cistanche tubulosa* extract provided in one of the embodiments of the present invention.

The inventors of the present invention further found that, in all of the ingredients of the *Cistanche tubulosa* extract, isoacteoside itself can effectively protect muscle cells against injury, and thus can be used for protecting muscles. Isoacteoside has the effect of treating and/or delaying muscle loss. Without being limited by the theory, it is believed that isoacteoside can effectively regulate, treat, and/or delay muscle loss caused by at least one of the following: aging, disease, and cachexia. Therefore, the present invention also provides uses of isoacteoside and/or a pharmaceutically acceptable salt of isoacteoside in protecting muscles, comprising a use of isoacteoside and/or a pharmaceutically acceptable salt of isoacteoside in the manufacture of a medicament or a food product for protecting muscles, a method of protecting muscles comprising administrating isoacteoside and/or a pharmaceutically acceptable salt of isoacteoside to a subject in need, and a food product or a pharmaceutical composition comprising isoacteoside and/or a pharmaceutically acceptable salt of isoacteoside.

The isoacteoside and/or a pharmaceutically acceptable salt of isoacteoside are preferably to be used in the form of a plant extract; and more preferably, they are used in the form of a *Cistanche tubulosa* extract, especially in the form of a polar solvent extract of *Cistanche tubulosa*.

Depending on the desired administration manner, the pharmaceutical composition or medicament according to the present invention may be provided in any suitable form without specific limitations. For example, the pharmaceutical composition or medicament can be administered by an oral or parenteral (such as subcutaneous, intravenous, intramuscular, peritoneal, or nasal) route to a subject in need, but administration is not limited thereby. Depending on the form and purpose, suitable carriers can be chosen and used to provide the pharmaceutical composition or medicament, wherein the carriers include excipients, diluents, auxiliaries, stabilizers, absorbent retarders, disintegrants, hydrotropic agents, emulsifiers, antioxidants, adhesives, binders, tackifiers, dispersants, suspending agents, lubricants, hygroscopic agents, etc.

As a dosage form suitable for oral administration, the pharmaceutical composition or medicament provided by the present invention may comprise any pharmaceutically acceptable carrier that will not adversely affect the desired effects of the active ingredient (i.e., the *Cistanche tubulosa* extract or isoacteoside). For example, the pharmaceutically acceptable carrier can be water, saline, dextrose, glycerol, ethanol or its analogs, cellulose, starch, sugar bentonite, and combinations thereof. The pharmaceutical composition or medicament can be provided in any suitable form for oral administration, such as in the form of a tablet (e.g., dragee), a pill, a capsule, granules, a pulvis, a fluidextract, a solution, syrup, a suspension, a tincture, etc.

As for the form of injection or drip suitable for subcutaneous, intravenous, intramuscular, or peritoneal administration, the pharmaceutical composition or medicament provided by the present invention may comprise one or more ingredient(s), such as an isotonic solution, a salt-buffered saline (e.g., phosphate-buffered saline or citrate-buffered saline), a hydrotropic agent, an emulsifier, 5% sugar solution, and other carriers to provide the pharmaceutical composition or medicament as an intravenous infusion, an emulsified intravenous infusion, a powder for injection, a suspension for injection, or a powder suspension for injection, etc. Alternatively, the pharmaceutical composition or medicament may be prepared as a pre-injection solid. The pre-injection solid can be provided in a form which is soluble in other solutions or suspensions, or in an emulsifiable form. A desired injection is provided by dissolving the pre-injection solid in other solutions or suspensions or emulsifying it prior to being administered to a subject in need.

Optionally, the medicament provided by the present invention may further comprise a suitable amount of additives, such as a flavoring agent, a toner, or a coloring agent for enhancing the palatability and the visual perception of the pharmaceutical composition or medicament, and/or a buffer, a conservative, a preservative, an antibacterial agent, or an antifungal agent for improving the stability and storability of the pharmaceutical composition or medicament. In addition, the pharmaceutical composition or medicament may optionally further comprise one or more other active ingredient(s) (such as vitamin D, vitamin B1, vitamin B2, nicotine, biotin, pantothenic acid, calcium, iodine, magnesium, zinc, proteins, etc.), or be used in combination with a medicament comprising one or more other active ingredients, to further enhance the effects of the pharmaceutical composition or medicament, or to increase the application flexibility and adaptability of the preparation thus provided, as long as the other active ingredients do not adversely affect the desired effects of the active ingredient of the present invention (i.e., the *Cistanche tubulosa* extract or isoacteoside).

Depending on the need, age, body weight, and health conditions of the subject, the pharmaceutical composition or medicament provided by the present invention may be dosed with various administration frequencies, such as once a day, multiple times a day, or once every few days, etc. For example, when the pharmaceutical composition or medicament is applied orally to a subject for protecting muscles, the dosage of the pharmaceutical composition or medicament is about 0.5 mg (as the *Cistanche tubulosa* extract)/kg-body weight to about 1000 mg (as the *Cistanche tubulosa* extract)/kg-body weight per day, preferably about 2.5 mg (as the *Cistanche tubulosa* extract)/kg-body weight to about 1000 mg (as the *Cistanche tubulosa* extract)/kg-body weight per day, and more preferably about 5 mg (as the *Cistanche tubulosa* extract)/kg-body weight to about 500 mg (as the *Cistanche tubulosa* extract)/kg-body weight per day. Alternatively, the dosage of the pharmaceutical composition or medicament is about 0.01 mg (as isoacteoside)/kg-body weight to about 100 mg (as isoacteoside)/kg-body weight per day, preferably about 0.03 mg (as isoacteoside)/kg-body weight to about 70 mg (as isoacteoside)/kg-body weight per day, and more preferably about 0.05 mg (as isoacteoside)/kg-body weight to about 50 mg (as isoacteoside)/kg-body weight per day. The unit "mg/kg-body weight" refers to the dosage required per kg-body weight of the subject.

The food product according to the present invention could be a health food, a nutritional supplement food or a special nutrition food, and it may be provided as dairy products, meat products, breadstuff, pasta, cookies, troche, capsule, fruit juices, teas, sport drinks, nutritional drinks, etc., but is not limited thereby. Preferably the food product according to the present invention is a health food.

Depending on the recommended daily dosage for the age, body weight and health conditions of the subject, the health food, nutritional supplement food and special nutrition food provided by the present invention can be taken in various frequencies, such as once a day, several times a day or once every few days, etc. The amount of the *Cistanche tubulosa* extract or isoacteoside in the health food, nutritional supplement food and special nutrition food provided by the present invention can be adjusted, preferably to the amount that should be taken daily, depending on the specific population.

The recommended daily dosage, use standards and use conditions for a specific population (e.g., pregnant woman, cancer patients, and heart failure patients), or the recommendations for a use in combination with another food product or medicament can be indicated on the exterior package of the health food, nutritional supplement food and/or special nutrition food provided by the present invention. Thus, it is suitable for the user to take the health food, nutritional supplement food and/or special nutrition food by him- or herself safely and securely without the instructions of a doctor, pharmacist, or related executive.

The present invention further provides a method for protecting muscles, comprising administering to a subject in need an effective amount of an active ingredient, wherein the active ingredient is a *Cistanche tubulosa* extract, isoacteoside and/or a pharmaceutically acceptable salt of isoacteoside. In the method for protecting muscles according to the present invention, the applied route, applied form, suitable dosage and use of the active ingredient in related treatment are all in line with the above description.

The present invention will be further illustrated in detail with specific examples as follows. However, the following examples are provided only for illustrating the present invention and the scope of the present invention is not limited thereby. The scope of the present invention will be indicated in the appended claims.

Example 1: Preparation and Ingredient Analysis of the *Cistanche tubulosa* Extract (CIS)

(1-1)

10 kg of the succulent stems of *Cistanche tubulosa* were sliced and soaked in a volume of water eight times that of the stems for 1 hour, stewed for 2 hours, and then filtered. The filtrate was collected. A volume of water six times that of dregs was added therein, and stewed twice at 1 hour each time, and then filtered. Three obtained filtrates were combined together, and then concentrated under reduced pressure at 50° C. to a specific gravity of 1.10. Thereafter, ethanol was added into the concentrate to a concentration of 60%, and refrigerated for 12 hours. The clear supernatant liquid was collected and concentrated under reduced pressure at 50° C. to provide a crude extract with a specific gravity of 1.10 and the ethanol was recovered. 6 kg of a crude extract were obtained. Then, the crude extract was dissolved in a volume of hot water having the same volume as the crude extract to provide a mixture. The mixture was injected into a macro-pore absorption resin column. The column was sequentially eluted with a volume of water four times that of the column and a volume of 40% ethanol five times that of the column. The water eluent was injected in the macro-pore absorption resin column, and then sequentially eluted with a volume of water three times that of the column and a volume of 40% ethanol four times that of the column. The obtained water eluent was discarded. The two obtained 40% ethanol eluents were collected and dried by concentration to provide about 1.1 kg of a *Cistanche tubulosa* extract (CIS).

(1-2)

The ingredients and the amount thereof in the *Cistanche tubulosa* extract obtained in the above (1-1) were analyzed by high performance liquid chromatography (HPLC) and a photodiode array (PDA) detector. The results show that the *Cistanche tubulosa* extract comprises echinacoside, acteoside (also called verbascoside), isoacteoside, etc. The said three ingredients comprise 25.4 wt. %, 3.8 wt. % and 4.1 wt. % of the *Cistanche tubulosa* extract, respectively.

Example 2: Establishment of a Model of Muscle Cell Injury

Tumor necrosis factor-α (TNF-α) is a pro-inflammatory cytokine with a molecular weight of 17,000. Human clinical data show that the level of TNF-α increases in patients with special diseases (e.g., cancer, AIDS or COPD), patients using anti-cancer drugs, and the elderly, such an increase often being accompanied by phenomena such as an increase in muscle catabolism (i.e., the decomposition and consumption of muscle) or muscle cell death. It was found by researchers that the increase of TNF-α level in an animal body by injecting TNF-α or a drug would cause muscle cell injury (including the metabolic imbalance of muscle protein, muscle cell apoptosis, etc.), and further cause muscle loss or muscle atrophy. To investigate the effects and mechanisms of the *Cistanche tubulosa* extract and the ingredients therein on protecting muscles, the inventors of the present invention established a muscle cell injury model with TNF-α.

Firstly, C2C12 cells (i.e., muscle cells of mice, purchased from ATCC) were cultured in H-DMEM medium (purchased from Sigma company) until 80% confluence was attained (i.e., the mixed cell monolayer comprises 80% of area). Thereafter, the cells were separated into four groups, and the mediums of all the groups were replaced by differentiation mediums supplemented with 2% horse serum. TNF-α (purchased from Sigma company) was then added into those mediums to provide final concentrations of 0, 2, 5, 10 ng/mL respectively. After being co-treated with the differentiation medium and TNF-α for 4 days, the mitochondrial membrane potential (MMP) and intracellular reactive oxidative stress (ROS) of the C2C12 cells were measured to serve as the index for model evaluation. Accordingly, a TNF-α induced muscle cell injury model was established. Finally, the group that was not treated with TNF-α (i.e., the concentration of TNF-α was 0 ng/mL) served as a basis for calculating the relative MMPs and intracellular ROSs of the other groups. The results are shown in FIG. 1 (all the data are presented as average values±SEM, n=6, analyzed with a t-test, *$p<0.05$, ***$p<0.001$).

Figure 1:
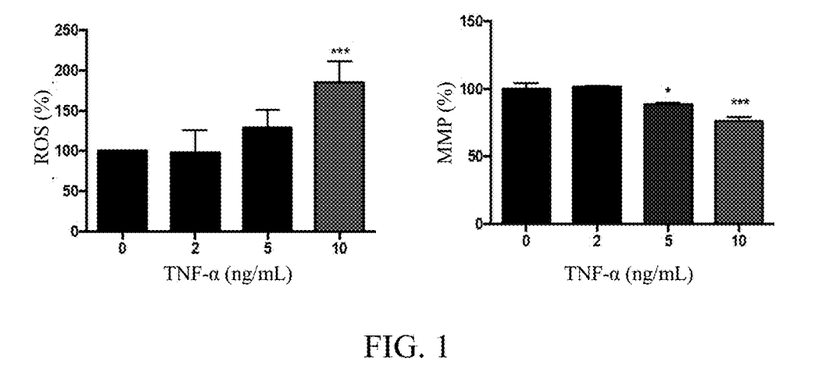
FIG. 1 illustrates the effects of Tumor necrosis factor-α (TNF-α) on the mitochondrial membrane potential (MMP) and the intracellular reactive oxidative stress (ROS) of the C2C12 cells.

As shown in FIG. 1, the MMP in the C2C12 cells being treated with 5 ng/mL of TNF-α significantly decreased, and the ROS in the cells slightly increased. Additionally, regarding the cells being treated with 10 ng/mL of TNF-α, the MMP in the cells significantly decreased and the ROS in the cells significantly increased. Therefore, 10 ng/mL was chosen as the experimental concentration of TNF-α for inducing muscle cell injury in the following experiments.

Example 3: Use Concentration of the *Cistanche tubulosa* Extract

*Cistanche tubulosa* extract obtained from Example 1 was dissolved in dimethyl sulfoxide (DMSO; purchased from Sigma company) to prepare the *Cistanche tubulosa* extract solution. C2C12 cells were cultured in H-DMEM medium until 80% confluence was attained. Thereafter, the cells were separated into eight groups, and the mediums of all the groups were replaced by differentiation mediums supplemented with 2% horse serum. The said *Cistanche tubulosa* extract solution with different concentrations were then added into those mediums to provide final concentrations of 0, 1, 5, 10, 50, 100, 500 or 1000 μg/mL respectively. After being co-treated with the differentiation medium for 24 hours, the survival rates (measured with MTT assay) and MMPs of the C2C12 cells were measured. The group that was not treated with the *Cistanche tubulosa* extract (i.e., the concentration of the *Cistanche tubulosa* extract was 0 ng/mL) served as a basis for calculating the relative survival rates and MMPs of the other groups to evaluate the cytotoxicity of *Cistanche tubulosa* extract on C2C12 cells and determine the appropriate concentration range and maximal dose for using the *Cistanche tubulosa* extract. The results are shown in FIG. 2 (all the data are presented as average values±SEM, n=6).

Figure 2:
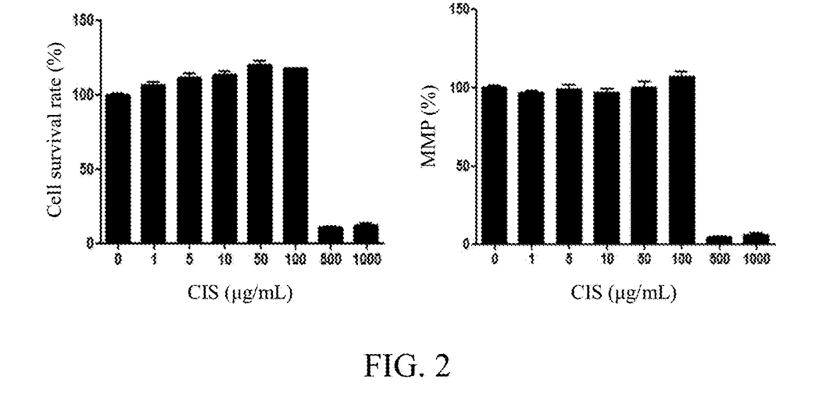
FIG. 2 illustrates the effects of the *Cistanche tubulosa* extract on the survival rate and the MMP of C2C12 cells.

As shown in FIG. 2, the cell survival rate and the MMP of C2C12 cells treated with 500 μg/mL of *Cistanche tubulosa* extract both significantly decreased. Therefore, the appropriate concentration for using the *Cistanche tubulosa* extract ranges from 1 to 500 μg/mL, and preferably from 1 to 100 μg/mL.

Example 4: Effects of the *Cistanche tubulosa* Extract on Protecting Muscle Cells Against Injury C2C12 cells were cultured in H-DMEM medium until 80% confluence was attained. Thereafter, the cells were separated into eleven groups, wherein seven groups thereof were provided with the *Cistanche tubulosa* extract (CIS) solution (dissolved in DMSO) to provide final concentrations of 0, 1, 5, 10, 50, 100, 500 μg/mL, respectively, and then pre-treatment was carried out for 6 hours; the other three groups were provided with branched chain amino acids (BCAA; served as a positive control) to provide final concentrations of 0.1, 1 or 10 μg/mL respectively, and then pre-treatment was carried out for 6 hours; thereafter, the mediums of the above ten groups (seven groups provided with CIS and three groups provided with BCAA) were replaced by differentiation mediums supplemented with 2% horse serum, and TNA-α was then added into those mediums to provide a final concentration of 10 ng/mL, and then co-treated with differentiation medium for 4 days; the last group served as a control group, which was not treated with the *Cistanche tubulosa* extract, BCAA, or TNA-α. Finally, the survival rates, MMPs and intracellular ROSs of the C2C12 cells in each group were measured. The control group served as a basis for calculating the relative survival rates, MMPs, and intracellular ROSs of the other groups to determine the effective concentration of *Cistanche tubulosa* extract for providing a protective effect against the TNF-α induced muscle cell injury. The results are shown in FIG. 3 and FIG. 4 (all the data are presented as average values±SEM, n=6, analyzed with a t-test, *p<0.05, p<0.01, *p<0.001).

Figure 3:
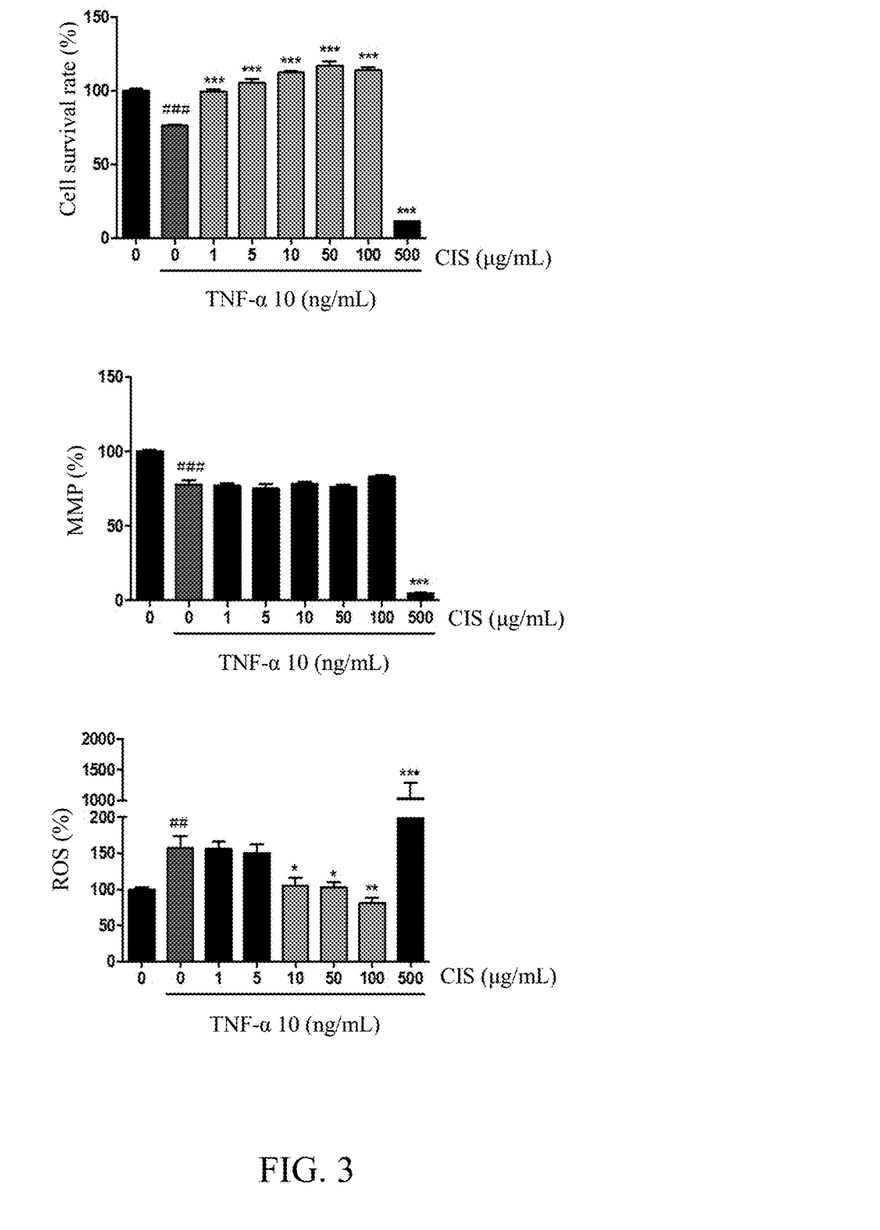
FIG. 3 illustrates the effect of the *Cistanche tubulosa* extract on the survival rate, MMP, and intracellular ROS of the C2C12 cells with TNF-α induced injury.

As shown in FIG. 3, in the TNF-α induced cell injury group, when pre-treated with *Cistanche tubulosa* extract ranging from 0 to 50 μg/mL, the survival rates of C2C12 cells gradually increased along with the increase in the concentration of *Cistanche tubulosa* extract, while the MMPs did not vary significantly. With respect to the intracellular ROS, the ROS in the cells pre-treated with 10 μg/mL of *Cistanche tubulosa* extract decreased to be equivalent to that in the cells of the control group (without TNF-α induced injury), while the ROS of the cells decreased more significantly when pre-treated with the *Cistanche tubulosa* extract at concentration of 50 μg/mL or 100 μg/mL.

Figure 4:
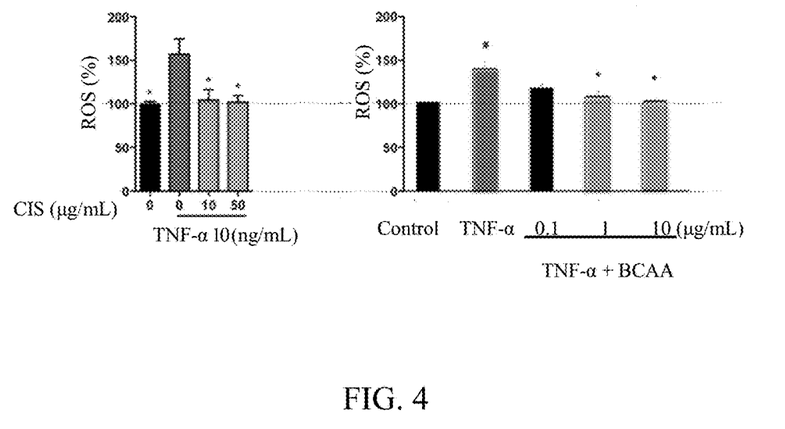
FIG. 4 illustrates the effect of the *Cistanche tubulosa* extract and branched chain amino acid (as a positive control) on the intracellular ROS of the C2C12 cells with TNF-α induced injury.

As shown in FIG. 4, on the basis of the ROS, the protective effects provided by 10 to 50 μg/mL of *Cistanche tubulosa* extract on C2C12 cells with TNF-α induced injury were comparable to those provided by the positive control group (i.e., BCAA).

Given the above, 10 to 50 μg/mL of *Cistanche tubulosa* extract is effective in providing significant protective effects for muscle cells, which can effectively decrease the TNF-α induced muscle cell injury. Therefore, 10 μg/mL and 50 μg/mL were chosen as the pre-treating concentrations of the *Cistanche tubulosa* extract in the following experiments.

Example 5: Effects of the *Cistanche tubulosa* Extract on Ameliorating the Glycolytic Capacity of the Injured Muscle Cells C2C12 cells were cultured in H-DMEM medium until 80% confluence was attained. Thereafter, the cells were separated into four groups and treated as follows:
(1) Control group: cells were cultured in H-DMEM medium for 6 hours; thereafter the medium was replaced by a differentiation medium supplemented with 2% horse serum.
(2) TNF-α group: cells were cultured in H-DMEM medium for 6 hours; thereafter the medium was replaced by a differentiation medium supplemented with 2% horse serum, and TNF-α was then added into the medium to provide a final concentration of 10 ng/mL.
(3) TNF-α+10CIS group: the *Cistanche tubulosa* extract (CIS) solution (dissolved in DMSO) was added into H-DMEM medium to provide a final concentration of 10 μg/mL. The cells were pre-treated with the above medium for 6 hours. Thereafter, the medium was replaced by a differentiation medium supplemented with 2% horse serum, and TNF-α was added into the medium to provide a final concentration of 10 ng/mL.
(4) TNF-α+50CIS group: the *Cistanche tubulosa* extract solution (dissolved in DMSO) was added into H-DMEM medium to provide a final concentration of 50 μg/mL. The cells were pre-treated with the above medium for 6 hours. Thereafter, the medium was replaced by a differentiation medium supplemented with 2% horse serum, and TNF-α was added into the medium to provide a final concentration of 10 ng/mL.

After the mediums of each group were replaced by differentiation mediums supplemented with 2% horse serum (depending on the groups, TNF-α was added or not), cell samples for each group were taken from the mediums. Thereafter, cell samples for each group were taken every 9 minutes. After the third sampling, glucose was added into the medium to carry out a co-treatment. Next, after the sixth sampling, oligomycin (oligo; purchased from Sigma company) was added into the medium to carry out a co-treatment. Thereafter, after the ninth sampling, 2-deoxy-glucose (2-DG; purchased from Sigma company) was added into the medium to carry out a co-treatment. Cell samples for each group were taken from the mediums for another three times after the addition of 2-deoxy-glucose. Finally, the extracellular acidification rates (ECAR) of C2C12 cells at each sampling point were measured. The results are shown in FIG. 5A and FIG. 5B.

The ECAR can indirectly show the glycolytic capacity of the cells, wherein the amount of pyruvic acid produced by glycolysis is reflected in the ECAR value. The glycolysis reaction of the cells was lower before the addition of glucose (the sampling points were 0, 9, 18 minutes), therefore the ECAR value at that time was lower; the glycolysis reaction of cells increased after the addition of glucose (the sampling points were 27, 36, 45 minutes), and thus the ECAR value increased accordingly. Because the oligomycin is a kind of ATP synthase inhibitor, the oxidative phosphorylation of ATP in the cells would be inhibited after the addition of oligomycin (the sampling points were 54, 63, 72 minutes), thus the cells relied completely on glycolysis to provide energy at that time, resulting in an significant increase of the ECAR value, wherein the increased value represents the glycolytic potential (i.e., the additional glycolysis capacity in the cells as compared to the last stage) and the total value represents the maximal glycolytic capacity of cells. After the addition of 2-deoxy-glucose (the sampling points were 81, 90, 99 minutes), the 2-deoxy-glucose would compete with the glucose leading to a block in the glycolysis reaction, in which the ECAR value represents the acid produced via the acid production mechanisms of cells other than glycolysis.

Figure 5A:
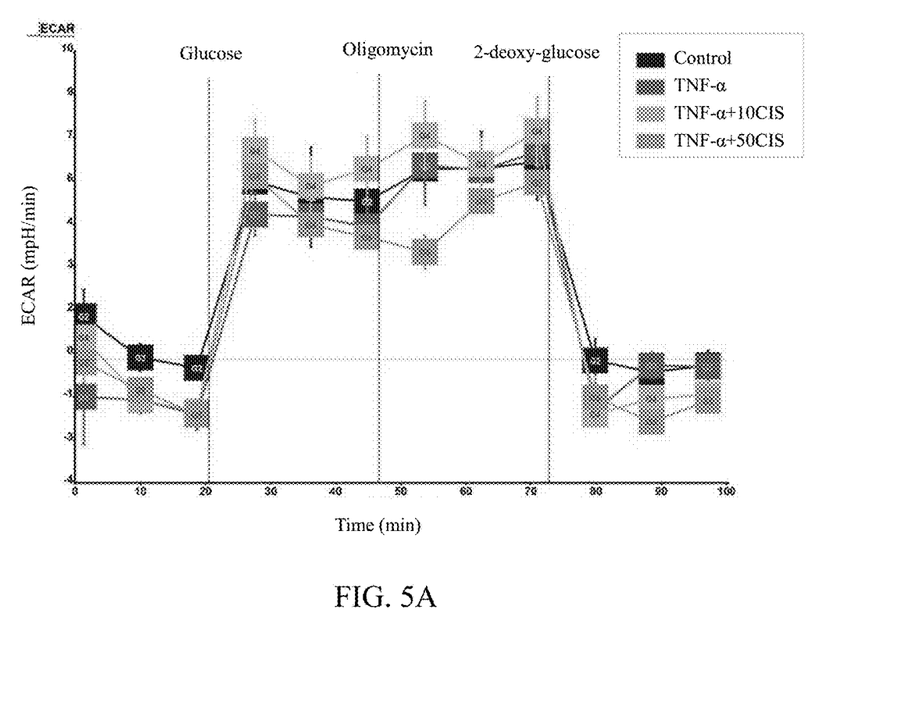
FIGS. 5A and 5B illustrate the effects of the *Cistanche tubulosa* extract on the glycolytic capacities of the C2C12 cells with TNF-α induced injury.
Figure 5B:
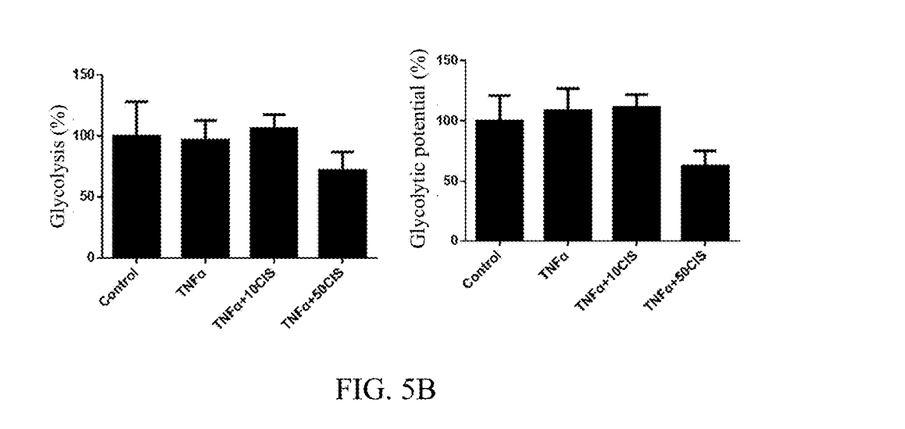

As shown in FIG. 5A and FIG. 5 B, the TNF-α induced C2C12 cell injury includes a decrease in the glycolysis capacity. As compared to the C2C12 cells that were not pre-treated with the *Cistanche tubulosa* extract (i.e., the TNF-α group), the C2C12 cells being pre-treated with 10 μg/mL *Cistanche tubulosa* extract (i.e., the TNF-α+10CIS group) had a higher glycolysis capacity. The results show that the *Cistanche tubulosa* extract can effectively ameliorate the decrease in the glycolysis capacity in muscle cells induced by TNF-α. Therefore, the *Cistanche tubulosa* extract has a protective effect on the muscle cells, and can effectively protect muscle cells against injury.

Example 6: Effects of the *Cistanche tubulosa* Extract on Ameliorating the Mitochondrial Respiratory Capacity of the Injured Muscle Cells C2C12 cells were cultured in H-DMEM medium until 80% confluence was attained. Thereafter, the cells were separated into four groups (i.e., control group, TNF-α group, TNF-α+10CIS group and TNF-α+50CIS group), and the mediums of each group were replaced by differentiation mediums supplemented with 2% horse serum in the manner described in Example 5 (depending on the groups, TNF-α was added or not).

After the mediums of each group were replaced by differentiation mediums supplemented with 2% horse serum (depending on the groups, TNF-α was added or not), cell samples for each group were taken from the mediums. Thereafter, cell samples for each group were taken every 9 minutes. After the third sampling, oligomycin (oligo) was added into the medium to carry out a co-treatment. Next, after the sixth sampling, carbonylcyanide-p-trifluoromethoxuphenylhydrazone (FCCP) was added into the medium to carry out a co-treatment. Thereafter, after the ninth sampling, a respiratory chain (electron transport chain) inhibitor, antimycin A (anti-A), was added into the mediums. Cell samples for each group were taken from the mediums for another three times after the addition of antimycin A. Finally, the mitochondrial oxygen consumption rates (OCR) of the C2C12 cells at each sampling point were measured. The results are shown in FIG. 6A and FIG. 6B.

The OCR value shown before the addition of oligomycin (the sampling points were 0, 9, 18 minutes) represents the basal level of oxygen consumption of the cells (reflecting the basal respiratory capacity of the cells) including oxygen consumed by the mitochondrial oxidative phosphorylation and proton leakage. Because oligomycin would inhibit the ATP synthase, the level of reduced oxygen consumption after the addition of oligomycin (the sampling points were 27, 36, 45 minutes) represents the oxygen consumed by the cells for ATP synthesis before the addition of oligomycin, which indirectly represents the amount of ATP produced by cells at a basal condition. Carbonylcyanide-p-trifluoromethoxuphenylhydrazone (FCCP), a kind of uncoupling agent, served as a proton carrier that carries a massive quantity of protons to reflux into the matrix of mitochondria, which causes a neutralization of pH gradient and massive oxygen consumption; however, this kind of proton reflux does not get through the ATP synthase and therefore does not form ATP. Therefore, the level of increased consumption of oxygen after the addition of FCCP (the sampling points were 54, 63, 72 minutes) represents the maximal oxygen consumption capacity of the mitochondria, which indirectly represents the maximal respiratory capacity of the cells; after the addition of antimycin A (the sampling points were 81, 90, 99 minutes), the mitochondrial respiratory chain was completely blocked, and the results measured at that time were the background values.

Figure 6A:
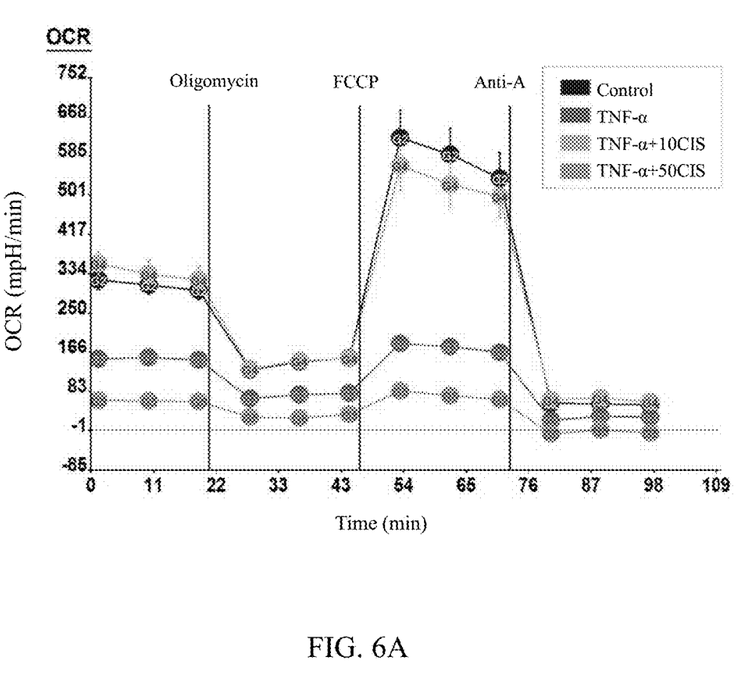
FIGS. 6A and 6B illustrate the effects of the *Cistanche tubulosa* extract on the mitochondrial respiratory capacities of the C2C12 cells with TNF-α induced injury.
Figure 6B:
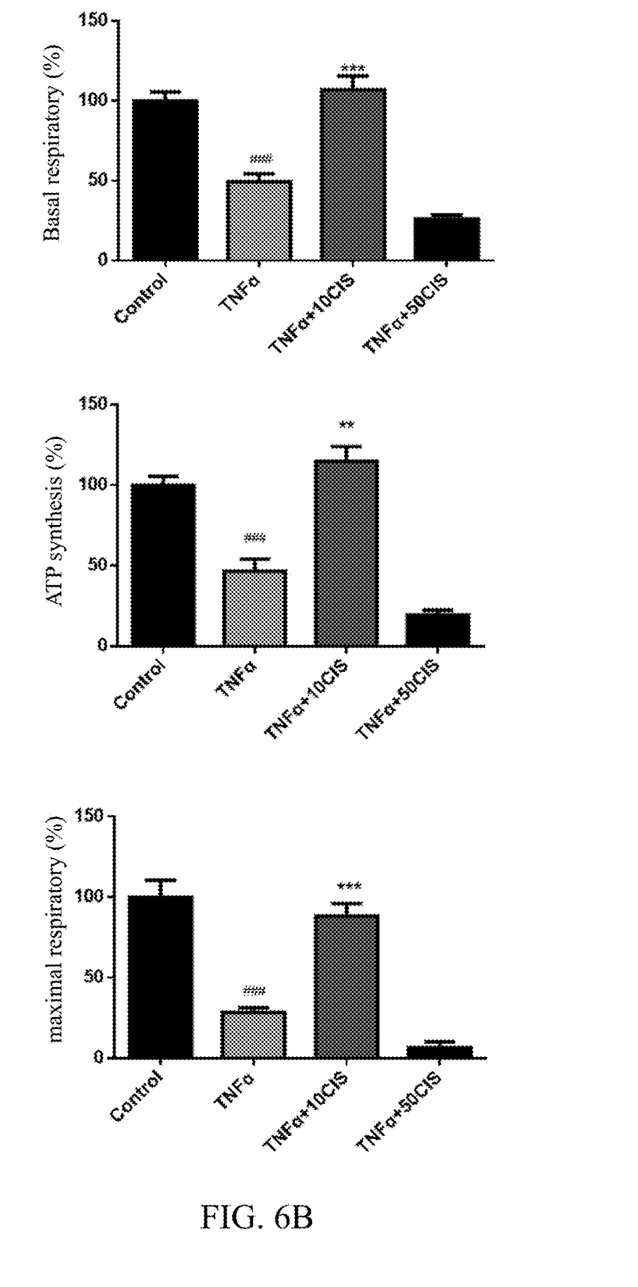

As shown in FIG. 6A and FIG. 6B, the TNF-α induced C2C12 cell injury includes a decrease of respiratory capacity. As compared to the C2C12 cells that were not pre-treated with the *Cistanche tubulosa* extract (i.e., the TNF-α group), the C2C12 cells pre-treated with 10 μg/mL *Cistanche tubulosa* extract (i.e., the TNF-α+10CIS group) had a higher respiratory capacity. The results show that the *Cistanche tubulosa* extract can effectively ameliorate the decrease of mitochondrial respiratory capacity in muscle cells induced by TNF-α. Therefore, the *Cistanche tubulosa* extract has a protective effect on the muscle cells, and can effectively protect muscle cells against injury.

Example 7: Effects of the Echinacoside, Verbascoside and Isoacteoside on Protecting Muscle Cells Against Injury According to the results of Example 1, echinacoside (Ech), verbascoside (VB) and isoacteoside (Iso) are the main ingredients of the *Cistanche tubulosa* extract. To investigate whether the echinacoside, verbascoside and isoacteoside have the effect of protecting muscles, the echinacoside, verbascoside and isoacteoside (all purchased from ChromaDex company, U.S.) were dissolved in DMSO to provide a echinacoside solution, a verbascoside solution and a isoacteoside solution. C2C12 cells were cultured in H-DMEM medium until 80% confluence was attained. Thereafter, the cells were separated into eighteen groups and treated as follows:

(1) Control group: cells were cultured in H-DMEM medium for 6 hours; thereafter the medium was replaced by a differentiation medium supplemented with 2% horse serum, and the cells were cultured for 4 days.

(2) TNF-α group: cells were cultured in H-DMEM medium for 6 hours; thereafter the medium was replaced by a differentiation medium supplemented with 2% horse serum, and TNF-α was then added into the medium (the final concentration was 10 ng/mL) to carry out a co-treatment for 4 days.

(3) TNF-α+echinacoside group (6 groups): the echinacoside solution was added into H-DMEM mediums to provide final concentrations of 1, 5, 10, 50, 100, or 500 μg/mL, respectively. The cells were pre-treated with the above mediums for 6 hours. Thereafter, the mediums were replaced by differentiation mediums supplemented with 2% horse serum, and TNF-α was then added into the mediums (the final concentration was 10 ng/mL) to carry out co-treatments for 4 days.

(4) TNF-α+verbascoside group (5 groups): the verbascoside solution was added into H-DMEM mediums to provide final concentration of 1, 5, 10, 50, or 100 μg/mL, respectively. The cells were pre-treated with the above mediums for 6 hours. Thereafter, the mediums were replaced by differentiation mediums supplemented with 2% horse serum, and TNF-α was then added into the mediums (the final concentration was 10 ng/mL) to carry out co-treatments for 4 days.

(5) TNF-α+isoacteoside group (5 groups): the isoacteoside solution was added into H-DMEM mediums to provide final concentrations of 1, 5, 10, 50, or 100 μg/mL, respectively. The cells were pre-treated with the above mediums for 6 hours. Thereafter, the mediums were replaced by differentiation mediums supplemented with 2% horse serum, and TNF-α was then added into the mediums (the final concentration was 10 ng/mL) to carry out the co-treatments for 4 days.

The survival rate, MMP and intracellular ROS of the C2C12 cells in each group were measured. The control group served as a basis for calculating the relative survival rates, MMPs, and intracellular ROSs of the other groups to evaluate the protective effects of the echinacoside, verbascoside and isoacteoside on the injured muscle cells. The results are shown in FIG. 7A, FIG. 7B and FIG. 7C (all the data are presented as average values±SEM, n=6, analyzed with a t-test, ###p<0.001, *p<0.05, p<0.01, *p<0.001).

Figure 7A:
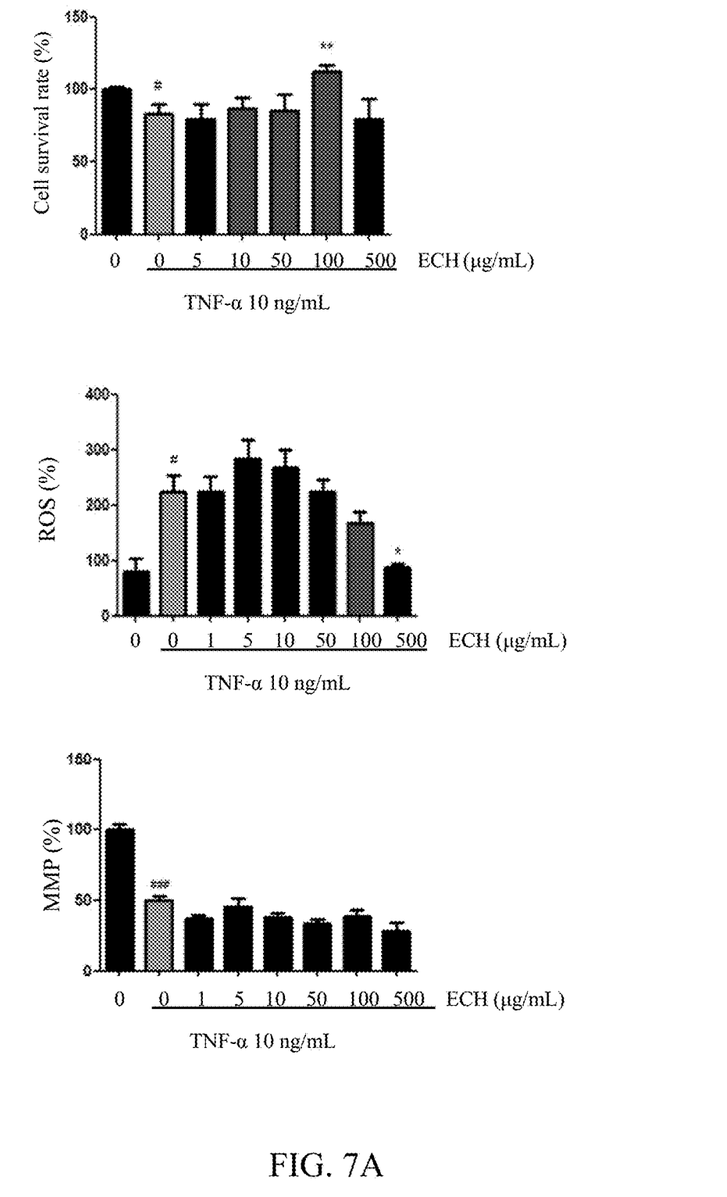
FIG. 7A illustrates the effects of echinacoside on the survival rate, MMP, and intracellular ROS of the C2C12 cells with TNF-α induced injury, respectively.
Figure 7B:
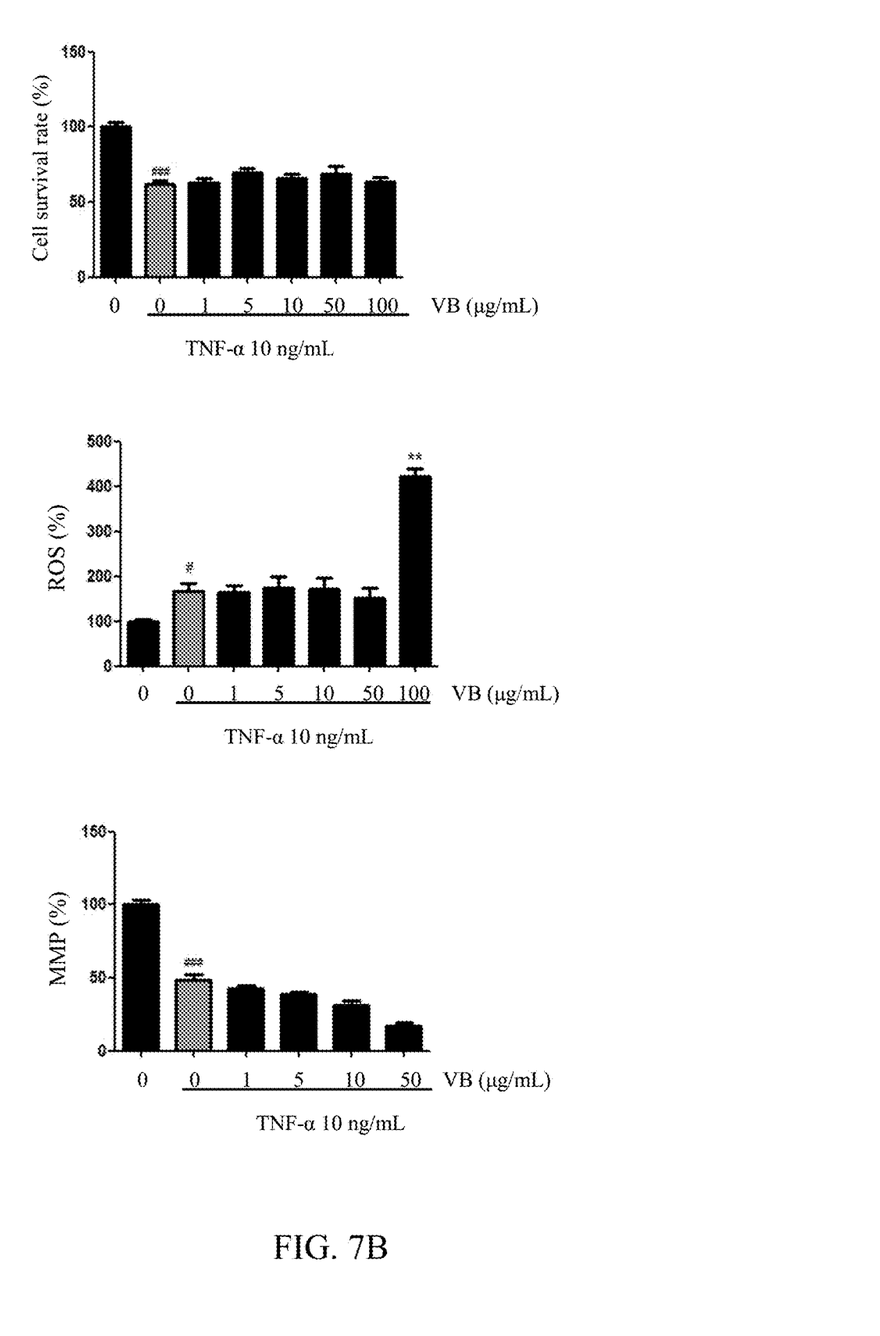
FIG. 7B illustrates the effects of verbascoside on the survival rate, MMP, and intracellular ROS of the C2C12 cells with TNF-α induced injury, respectively.

As shown in FIG. 7A, when the C2C12 cells were pre-treated with the echinacoside solutions having concentrations ranging from 5 to 500 μg/mL, the protective effect was not significant under a lower concentration. The protective effect only became significant when the concentration got up to 100 μg/mL. However, echinacoside did not exhibit protective effect on MMP and ROS. In another respect, as shown in FIG. 7B, when the C2C12 cells were pre-treated with the verbascoside solution having concentrations ranging from 1 to 100 μg/mL, verbascoside could not protect the C2C12 cells against TNF-α induced injury.

Figure 7C:
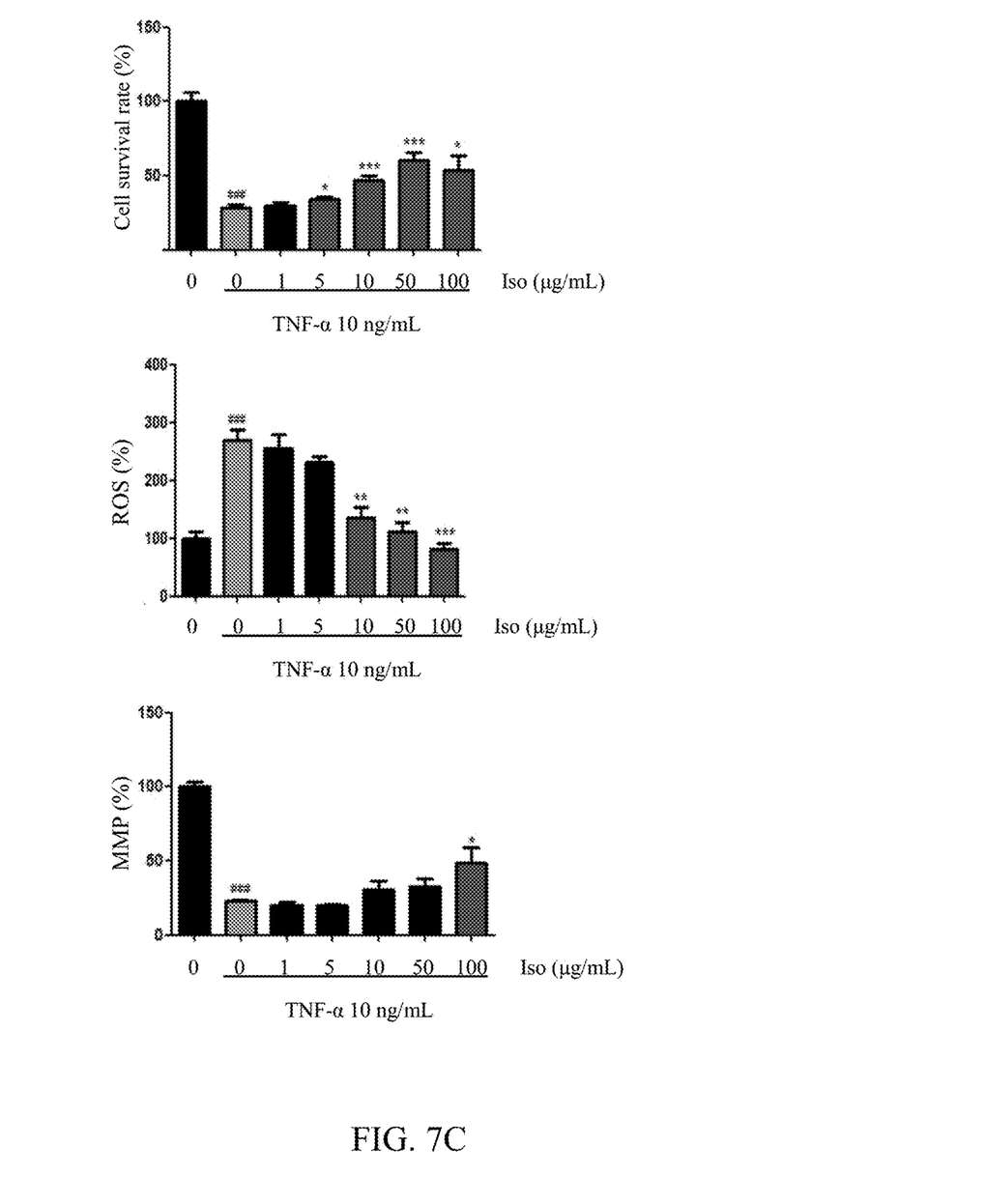
FIG. 7C illustrates the effects of isoacteoside on the survival rate, MMP, and intracellular ROS of the C2C12 cells with TNF-α induced injury, respectively.

As shown in FIG. 7C, when the C2C12 cells were pre-treated with the isoacteoside solution having concentrations ranging from 5 to 100 μg/mL, the survival rates of the C2C12 cells with TNF-α induced injury increased, which indicates that isoacteoside effectively decreased the TNF-α induced injury to the C2C12 cells. In another respect, when the C2C12 cells were pre-treated with the isoacteoside solution having a concentration of 100 μg/mL, the decrease in the MMP induced by TNF-α could be significantly ameliorated. In still another respect, when the C2C12 cells were pre-treated with the isoacteoside solution having concentrations ranging from 10 to 100 μg/mL, the intracellular ROS in the C2C12 cells with TNF-α induced injury significantly decreased. The above results indicate that isoacteoside can effectively decrease TNF-α induced muscle cell injury, and that it has a significantly protective effect. Therefore, isoacteoside is the effective ingredient of the *Cistanche tubulosa* extract.

Example 8: Molecular Mechanism of the *Cistanche tubulosa* Extract and the Ingredient Contained Therein in Protecting Muscles C2C12 cells were cultured in H-DMEM medium until 80% confluence was attained. Thereafter, the cells were separated into four groups (i.e., control group, TNF-α group, TNF-α+10CIS group and TNF-α+50CIS group) and the mediums of each group were replaced by differentiation mediums supplemented with 2% horse serum in the same manner described in Example 5 (depending on the groups, TNF-α was added or not). Thereafter, the cells were allowed to culture for 4 days.

After the incubation, the proteins of cells in each group were extracted. Thereafter, the expression level of proteins related to the mTOR/AMPK signaling pathway (which relates to the maintenance of energy balance in the cells) and the NF-κB/p-JNK signaling pathway (which relates to the inflammation reaction and protein degradation) were examined through a western blot. The results are shown in FIG. 8.

It was found by researchers that the protein degradation induced by TNF-α is due to the TNF-α induced IκBα degradation, which activates NFκB and makes it enter the cell nucleus to combine with genes of the ubiquitin-proteasome pathway related-proteins, thus promoting the transcription of those genes. The above causes an increase of the synthesis of ubiquitin-proteasome pathway related-proteins and further promotes a large degradation of muscle proteins. However, as shown in FIG. 8, the *Cistanche tubulosa* extract does not significantly inhibit the inflammation factor, NFκB.

Figure 8:
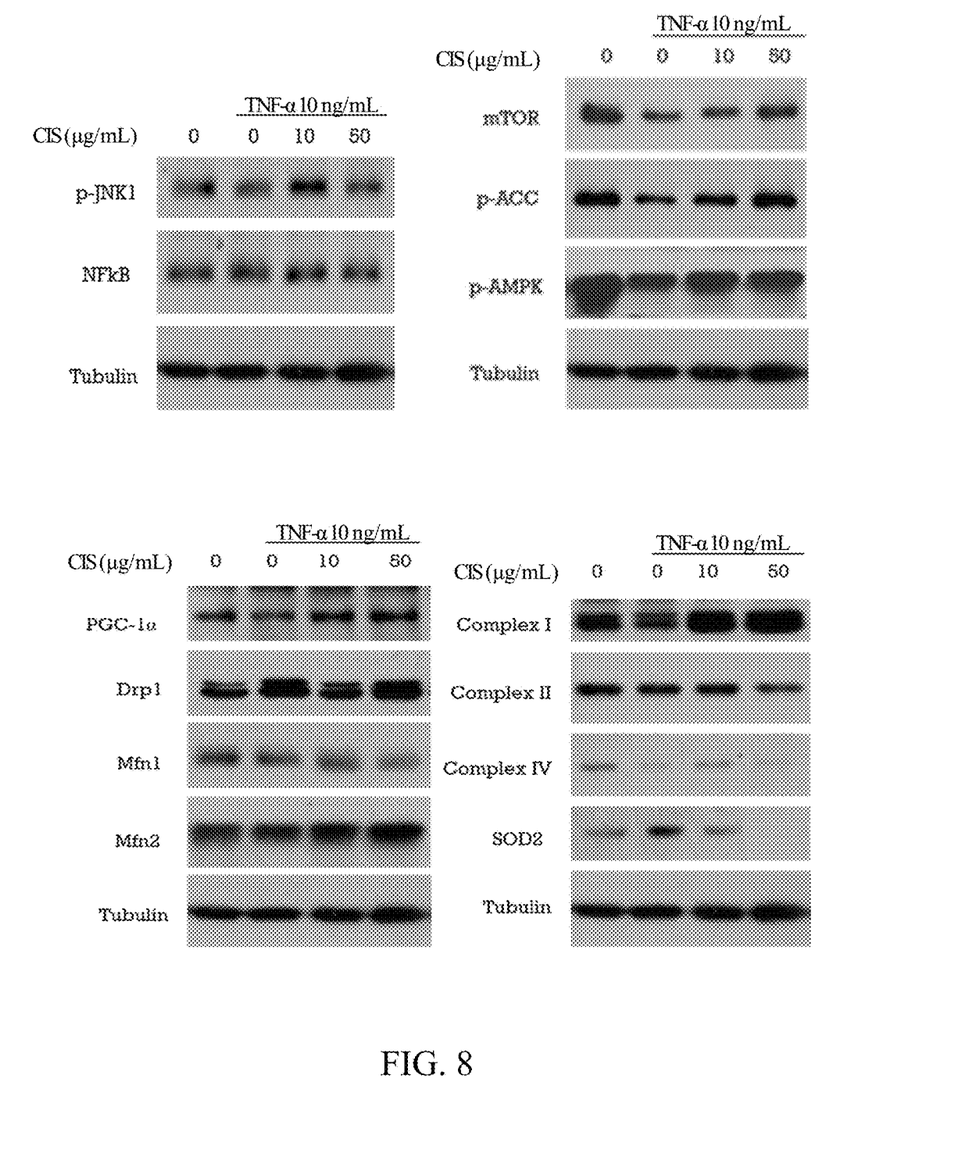
FIG. 8 illustrates the effects of the *Cistanche tubulosa* extract on the expression levels of the proteins related to the mTOR/AMPK signaling pathway and NFκB/p-JNK signaling pathway in the C2C12 cells with TNF-α induced injury.

As shown in FIG. 8, there were decreases in the protein expression levels of mTOR, AMPK, PGC-1α, MFN2 and mitochondrial Complex I in the TNF-α group, wherein the mitochondrial Complex I is an important enzyme in the mitochondrial respiratory chain, PGC-1α is a transcription factor that promotes the synthesis of mitochondria and oxidative energy metabolism in skeletal muscle cells, while MFN2 relates to the mitochondria fusion and exhibits a synergistic effect with PGC-1α on maintaining MMP and promoting oxidative phosphorylation. The above results show that the TNF-α induced muscle cell injury will affect the mTOR/AMPK signaling pathway, and thus breaks the cellular energy metabolic system.

In another aspect, as compared to the TNF-α group, the expression levels of PGC-1α, MFN2 and mitochondrial Complex I of the C2C12 cells pre-treated with the *Cistanche tubulosa* extract (i.e., the TNF-α+10CIS group and TNF-α+50CIS group) all significantly increased, which shows that the *Cistanche tubulosa* extract can start the mTOR/AMPK signaling pathway in the muscle cells. By expressing proteins such as PGC-1α and MFN2, the *Cistanche tubulosa* extract can stabilize the amount and activation of mitochondria, as well as repair the damage received by the cellular energy metabolic system (this function is similar to that of BCAA). Therefore, the protective mechanism of *Cistanche tubulosa* extract and ingredients contained therein on the muscle cells are relative to the anti-autophagy reaction and the promotion of cellular mitochondria production.

As shown in the above experimental results, the *Cistanche tubulosa* extract and isoacteoside contained therein both can effectively protect the injured muscle cells, which increases the muscle cell survival rate, inhibit the decrease of MMP and the increase of ROS, and maintain the intracellular mitochondria activity. Therefore, the *Cistanche tubulosa* extract and isoacteoside have good biological effects on ameliorating the oxidative stress and maintaining the mitochondria activity to the injured muscle cells. Additionally, the *Cistanche tubulosa* extract can restart the mTOR/AMPK signaling pathway in the injured muscle cells, which causes a rebound of the expression levels of downstream mitochondrial biosynthesis related-proteins (e.g., PGC-1α), mitochondria fusion related-molecules (e.g., MFN2), and mitochondrial proteins involved in the respiratory chain (e.g., Complex I), and thus recovers the energy metabolic capacity of muscle cells. This illustrates again that the *Cistanche tubulosa* extract and ingredients contained therein can effectively protect muscle cells against injury, and thus can be used for protecting muscles. The *Cistanche tubulosa* extract and the ingredients contained therein have the effects of treating and/or delaying muscle loss or muscle atrophy, and are useful for helping normal muscle contraction, maintaining normal muscle physiology, maintaining normal neuromuscular function, maintaining normal energy metabolism, or enhancing energy.

BRIEF DESCRIPTION OF REFERENCE NUMERALS

Not applicable.

What is claimed is:

1. A method of protecting muscles, comprising administering to a subject having muscle loss an effective amount of an active ingredient, wherein the active ingredient is isoacteoside and/or a pharmaceutically acceptable salt of isoacteoside, and is administered to the subject in an amount between about 0.01 mg/kg-body weight to about 100 mg/kg-body weight per day.

2. The method as claimed in claim 1, wherein the active ingredient is used in the form of a plant extract.

3. The method as claimed in claim 2, wherein the plant extract is a *Cistanche tubulosa* extract.

4. The method as claimed in claim 1, which is for protecting muscle cells against injury.

5. The method as claimed in claim 1, which is for regulating, treating, and/or delaying muscle loss caused by at least one of the following: aging, disease, and cachexia.

6. The method as claimed in claim 1, which is for helping normal muscle contraction, maintaining normal muscle physiology, maintaining normal neuromuscular function, maintaining normal energy metabolism, or enhancing energy.

* * * * *